United States Patent
Mukaide et al.

(10) Patent No.: US 8,532,257 B2
(45) Date of Patent: Sep. 10, 2013

(54) X-RAY IMAGING APPARATUS AND X-RAY IMAGING METHOD

(75) Inventors: Taihei Mukaide, Atsugi (JP); Kazunori Fukuda, Fujisawa (JP); Masatoshi Watanabe, Isehara (JP); Kazuhiro Takada, Kawasaki (JP); Takashi Noma, Hadano (JP)

(73) Assignee: Canon Kabushiki Kaisha, Tokyo (JP)

( * ) Notice: Subject to any disclaimer, the term of this patent is extended or adjusted under 35 U.S.C. 154(b) by 222 days.

(21) Appl. No.: 13/058,889

(22) PCT Filed: Nov. 29, 2010

(86) PCT No.: PCT/JP2010/071763
§ 371 (c)(1),
(2), (4) Date: Feb. 14, 2011

(87) PCT Pub. No.: WO2011/068230
PCT Pub. Date: Jun. 9, 2011

(65) Prior Publication Data
US 2011/0194674 A1 Aug. 11, 2011

(30) Foreign Application Priority Data
Dec. 4, 2009 (JP) .................. 2009-276521

(51) Int. Cl.
*G01N 23/04* (2006.01)

(52) U.S. Cl.
USPC ............................................ 378/62; 378/98.8

(58) Field of Classification Search
USPC ..................... 378/62, 147, 149, 156, 98.8
See application file for complete search history.

(56) References Cited

U.S. PATENT DOCUMENTS

| 5,812,629 A | * | 9/1998 | Clauser | 378/62 |
| 7,319,734 B2 | | 1/2008 | Besson et al. | 378/37 |
| 2003/0123611 A1 | | 7/2003 | Ohara et al. | 378/98.8 |
| 2010/0318302 A1 | | 12/2010 | Mukaide et al. | 702/28 |

FOREIGN PATENT DOCUMENTS

| EP | 1879020 | 1/2008 |
| JP | 2008-200357 | 9/2008 |
| JP | 2008-200358 | 9/2008 |
| JP | 2010-502977 | 1/2010 |
| WO | WO 2008/029107 | 3/2008 |

* cited by examiner

*Primary Examiner* — Courtney Thomas
(74) *Attorney, Agent, or Firm* — Fitzpatrick, Cella, Harper & Scinto (57) ABSTRACT

An X-ray imaging apparatus and an X-ray imaging method can alleviate the influence of scattered X-rays relative to the obtained image. A differential phase contrast image or a phase contrast image of a detection object is computed by using a splitting element and an exposure control unit that synchronizes the X-ray scanning speed and the image acquisition speed of a detecting unit.

13 Claims, 12 Drawing Sheets

X-RAY IMAGING APPARATUS AND X-RAY IMAGING METHOD

TECHNICAL FIELD

The present invention relates to an X-ray imaging apparatus and an X-ray imaging method.

BACKGROUND ART

Non-destructive testing methods using radiation have been and are being broadly employed in various fields extending from various industries to medical applications. An X-ray, for instance, is an electromagnetic wave with a wavelength of about 1 pm to 10 nm ($10^{-12}$ to $10^{-8}$m). X-rays having a short wavelength (about 2 keV~) are referred to as hard X-rays, whereas those having a long wavelength (about 0.1 keV to about 2 keV) are referred to as soft X-rays.

Absorption contrast techniques that are devised to exploit a difference of absorptive power relative to an X-ray by utilizing a high transmissivity of X-ray can find practical applications such as detection of internal fissures in steel materials and security measures including hand baggage security screenings. On the other hand, X-ray phase contrast imaging of detecting a phase shift of an X-ray caused by a detection object is effective with an object that provides little contrast attributable to X-ray absorption and hence shows a small density difference. Techniques that employ X-ray phase contrast imaging are being studied to find applications such as imaging polymer blends of polymer materials and medical applications.

Among various X-ray phase contrast imaging techniques, PATENT LITERATURE 1 listed below proposes a method that utilizes a refractive effect due to a phase shift caused by a detection object. With this method, an X-ray is generated by an X-ray source and irradiated onto a detection object. Then, the X-ray transmitted through the detection object is discretely focused to a pixel area covering two or more than two pixels on a two-dimensional detector by an X-ray optical means. With such a method, the position of the center of gravity of the focused X-ray can be obtained from the intensity distribution on the pixels covered by the focused X-ray. While the quantity of refraction of an X-ray due to a detection object is very small, the angle of refraction can be obtained by comparing the position of the center of gravity of the focused X-ray in a state where there is not any detection object and the position of the center of gravity in a state where there is a detection object and determining the quantity of discrepancy between the two positions. Then, as a result, an image relating to the phase shift of an X-ray due to the detection object can be obtained.

Additionally, since the above-described technique directly utilizes the refractive effect of a detection object on X-rays, it is characterized by not requiring highly coherent X-rays such as synchrotron radiations unlike many X-ray phase contrast imaging techniques.

CITATION LIST

Patent Literature

PATENT LITERATURE 1: Japanese Patent Application Laid-Open No. 2008-200358 Publication

SUMMARY OF INVENTION

Technical Problem

However, with the method described in PATENT LITERATURE 1, the entire surface of a detection object is irradiated with X-rays to produce scattered X-rays to a large extent, which adversely affect the quality of the image obtained by the measurement. Particularly, the influence of such scattered X-rays from the detection object is remarkable when the detection object has a large thickness, and becomes a serious problem in medical applications.

In view of the above-identified problems, it is therefore the object of the present invention to provide an X-ray imaging apparatus and an X-ray imaging method that can alleviate the influence of scattered X-rays relative to the obtained image as compared with the method described in PATENT LITERATURE 1.

Solution to Problem

In an aspect of the present invention, the above object is achieved by providing an X-ray imaging apparatus comprising: a splitting element that spatially splits an X-ray generated from an X-ray generating unit; a detecting unit that detects each intensity of the split X-rays split by the splitting element and transmitted through a detection object; a transport unit that moves the X-ray generating unit, the splitting element, the detection object or the detecting unit; a transport control unit that controls a scanning time of the X-rays irradiated onto the detection object by means of the transport unit; an exposure control unit that synchronizes the scanning time of the X-rays and an image acquisition time of the detecting unit; and a computing unit that computes a differential phase contrast image or a phase contrast image of the detection object from the information acquired by the detecting unit.

In another aspect of the present invention, the above object is achieved by providing an X-ray imaging method comprising: spatially splitting an X-ray generated from an X-ray generating unit by means of a splitting element; irradiating the spatially split X-rays onto a detection object, detecting the intensity of the X-rays transmitted through the detection object by a detecting unit, while synchronizing a scanning time of irradiating X-rays onto the detection object and an image acquisition time of the detecting unit; and computing a differential phase contrast image or a phase contrast image of the detection object from information acquired by the detecting unit.

Advantageous Effects of Invention

Thus, according to the present invention, there are provided an X-ray imaging apparatus and an X-ray imaging method that can alleviate the influence of scattered X-rays relative to the obtained image as compared with the method described in Patent Literature 1.

Further features of the present invention will become apparent from the following description of exemplary embodiments with reference to the attached drawings.

DESCRIPTION OF EMBODIMENTS

According to the present invention, an X-ray transmittance contrast image, a differential phase contrast image or a phase contrast image of a detection object is acquired from the information obtained by detecting, using a detecting unit, the intensity of the split X-rays split by a splitting element and transmitted through the detection object. Then, it is so arranged that each of the X-rays transmitted through the detection object is directed discretely in the direction area perpendicular to the optical axis direction onto a pixel area of two or more than two pixels of the detecting unit, which has a plurality of pixels. Additionally, it is so arranged that the scanning time of the X-rays irradiated onto the detection object and the image acquisition time of the detecting unit can be synchronized.

The expression the "X-ray scanning time" as used herein refers to the time necessary for scanning a region of the detection object that corresponds to a desired image acquisition region (one pixel, for example). Thus, when the X-ray source, the splitting element and the detector are moved while the detection object is rigidly secured, the X-ray scanning time is the moving time for moving the X-ray source 101 and so on for one pixel, for example. On the other hand, when the detection object is moved while the X-ray source, the splitting element and the detector are rigidly secured, the X-ray scanning time is the time necessary for moving the detection object 104 by one pixel, for example.

The expression the "image acquisition time of the detector" as used herein refers to the time necessary for acquiring an image of a desired image acquisition region (one pixel, for example). The image acquisition time is equal to the exposure time necessary for exposing the desired image acquisition region (one pixel, for example) to light.

Thus, if the X-ray scanning time is synchronized with the image acquisition time of the detector, an image of a part of the detection object can be picked up at clock time T1 by a first pixel of the detector and another image of the part same as the part of which an image is picked up by the first pixel can also be picked up at clock time T2 by a second pixel that is next to the first pixel.

With the above-described configuration, the volume in the detection object 104 that contributes to scattering can be reduced, to enable scattered X-rays relative to the image to be acquired to be reduced because minutely split X-rays are scanned.

Embodiment 1

A configuration example of an X-ray imaging apparatus that acquires an image from a phase shift of X-rays by using a splitting element and a two-dimensional detector will be described by way of Embodiment 1.

Figure 1:
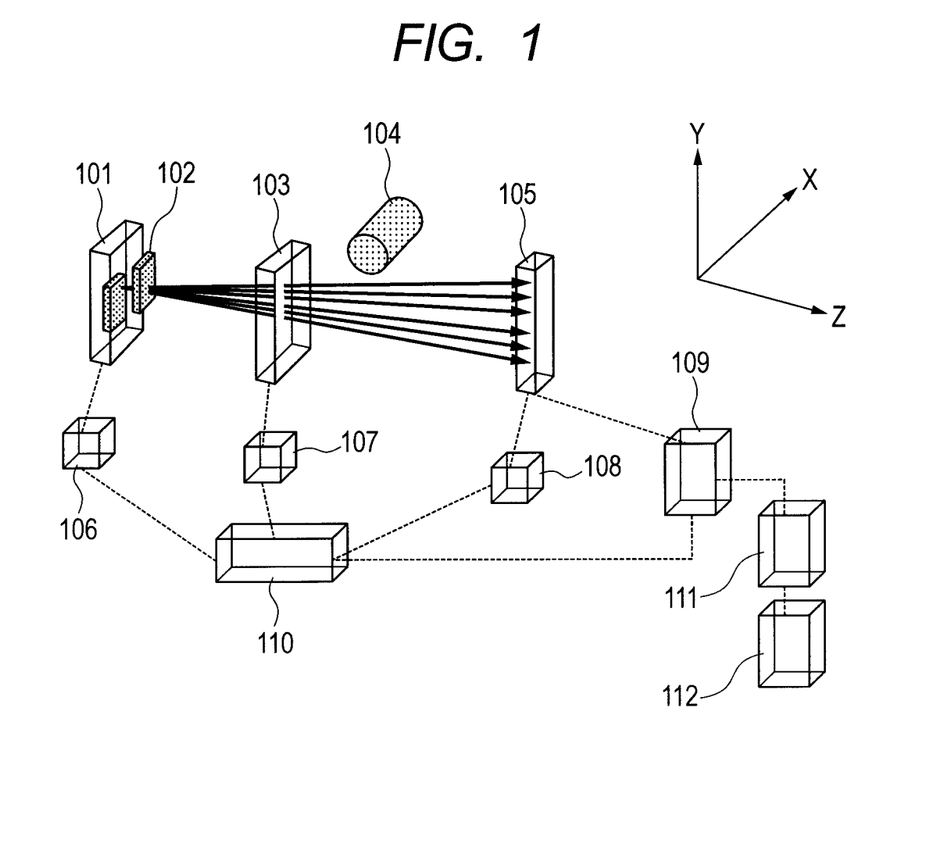
FIG. 1 is a schematic illustration of a configuration example of the X-ray imaging apparatus according to Embodiment 1 of the present invention.

FIG. 1 is a schematic illustration of a configuration example of the X-ray imaging apparatus of Embodiment 1. As shown in FIG. 1, the X-ray imaging apparatus of this embodiment includes an X-ray source 101 as X-ray generation source for generating an X-ray and irradiating the X-ray onto a detection object 104. A splitting element 103 and a detector 105 are arranged on the optical axis of the X-ray.

Divergence of the X-ray generated from the X-ray source 101 that is an X-ray generating unit is limited by means of a slit 102 or the like. The slit 102 may be integrally formed with the X-ray source 101. The X-rays whose divergence is limited are spatially split in the Y-direction and X-direction, which are perpendicular to the Z-direction, which agrees with the direction of the optical axis of the X-rays, by the splitting element 103 and some of the split X-rays are transmitted through a part of the detection object 104. Note that FIG. 1 shows an instance where the generated X-rays are spatially split in the Y-direction.

Figure 2:
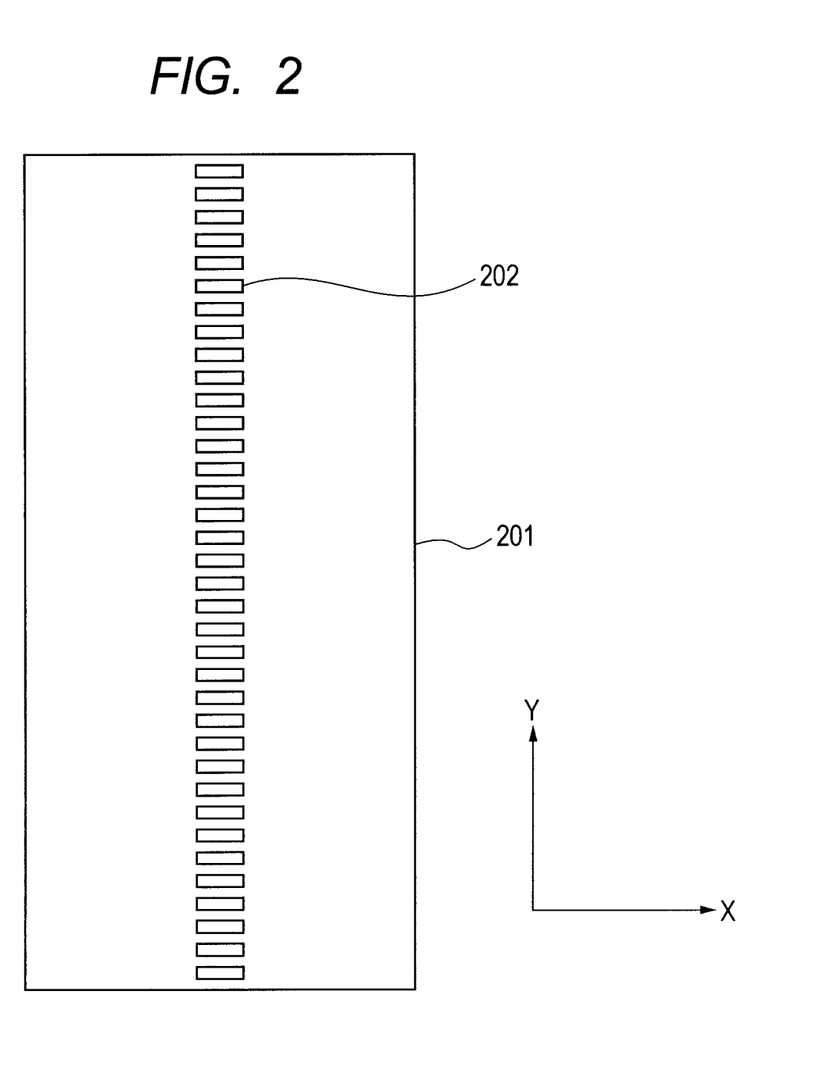
FIG. 2 is a schematic illustration of the splitting element of Embodiment 1.

FIG. 2 schematically illustrates the splitting element 103. Base material 201 of the splitting element 103 provides an effect of blocking X-rays and is made of Pt, Au, Pb, Ta, W or the like showing a high X-ray absorption factor or a compound of any of them. Alternatively, a plurality of splitting elements 103 of different sizes may be arranged with different intervals on the optical axis by taking divergence (the expansion factor) of X-rays into consideration.

The slit 102 limits the irradiation of an X-ray to within the base material 201. Holes 202 that allow X-rays to pass through are cut through the base material 201 periodically in the direction of the Y-axis, although the holes 202 may not necessarily be cut through the base material of the optical element so long as X-rays can be transmitted through them. While the holes 202 are provided as an array of slits to form a line and space pattern, they may alternatively be circular holes.

The X-rays produced as the generated X-rays are split by the splitting element 103 are refracted by the detection object 104. The X-rays that are transmitted through the detection object 104 are then irradiated onto detector 105 having a spatial resolution.

Figure 3:
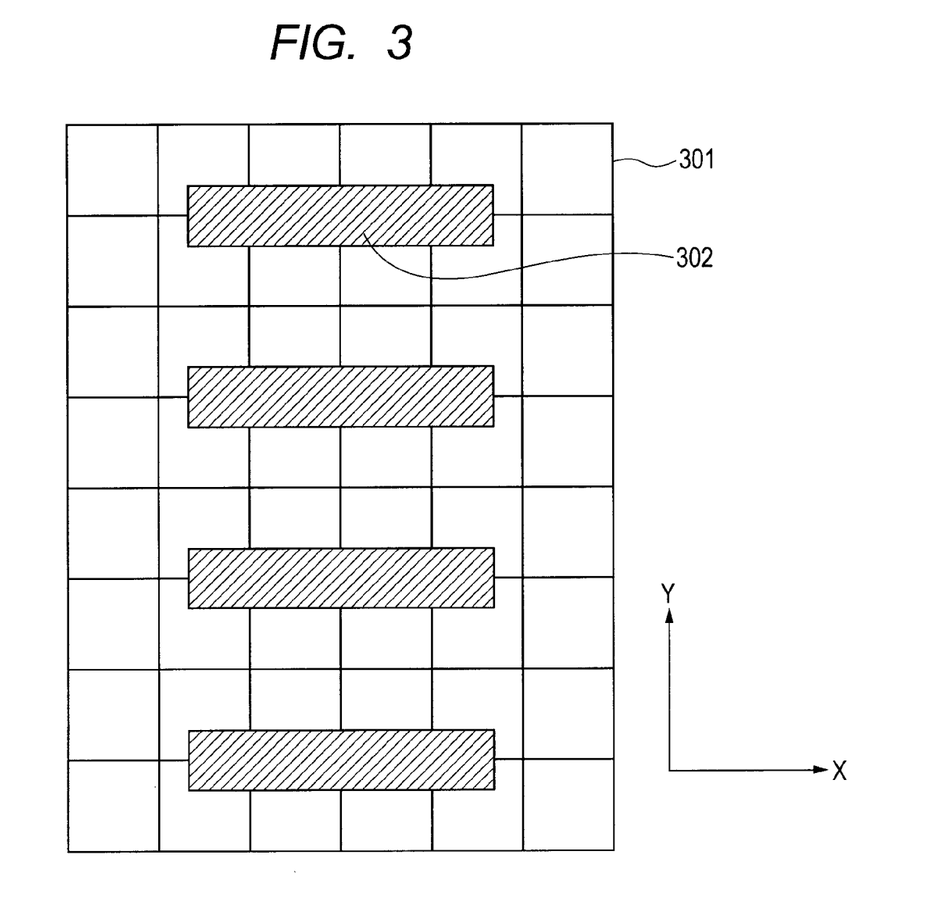
FIG. 3 is a schematic illustration of a part of the detector of Embodiment 1.

FIG. 3 schematically illustrates the detector 105. The detector 105 is formed by a plurality of pixels 301. Each of the X-rays 302 produced as the generated X-ray is split by the splitting element 103 is discretely irradiated over 2 pixels out of the pixels 301 that are arranged in the Y-direction.

The detector 105 detects the intensity of each of the irradiated X-rays at each of the pixels. The X-ray source 101, the splitting element 103 and the detector 105 have respective transport units 106, 107 and 108. The X-ray detector 105 has an exposure control unit 109 for controlling the image acquisition speed.

Thus, the transport control unit 110 and the exposure control unit 109 are operated to synchronize the moving time of the X-ray source 101, the splitting element 103 and the detector 105 in the X-direction and the image acquisition time of the detector 105 for each image acquisition in order to synchronize the scanning time of the X-rays irradiated onto the detection object and the image acquisition time of the detector. As a result, it is possible to obtain information on the entire detection object 104. The movements caused by the transport units 106, 107 and 108 may be circular movements along respective circles centered at the X-ray source 101.

Alternatively, the detection object 104 may be provided with a transport unit and the moving time of the detection object 104 on the X-axis and the image acquisition time of the detector 105 may be synchronized to obtain information on the entire detection object 104.

Furthermore, if the field of view of the detector 105 covers the region of observation of the detection object 104, the detector 105 may be rigidly held and information on the entire detection object 104 may be obtained by synchronizing the moving time of the X-ray source 101 and the splitting element 103 and the image acquisition time of the detector 105.

The information on the X-rays obtained by the detector 105 is numerically processed by the computing unit 111 and output to display unit 112 that may be a monitor.

The detection object 104 may be a human body or an object other than a human body such as an inorganic material or an inorganic/organic composite material.

Any of various detectors including those of the indirect type and those of the direct type may be used for the detector 105. Examples of detectors that can be used for the purpose of the present invention include X-ray flat panel detectors, X-ray CCD cameras and other direct conversion type two-dimensional X-ray detectors, X-ray line sensors and X-ray TDI (time delay integration) detectors.

An X-ray refraction lens array may be arranged between the detection object 104 and the detector 105. A number of X-ray refraction lenses having focusing power are arranged in an intra-planar direction cyclically with a predetermined period in an X-ray refraction lens array. The spot diameters of the X-rays on the detector 105 can be reduced by means of an X-ray refraction lens array to by turn boost the change in the intensity of each of the X-rays relative to a change of the incident position of the X-ray. Then, as a result, the quantity of refraction of the X-ray can be measured with a high sensitivity.

Now, detection of a phase shift of an X-ray caused by a detection object 104 will be described below.

Figure 4:
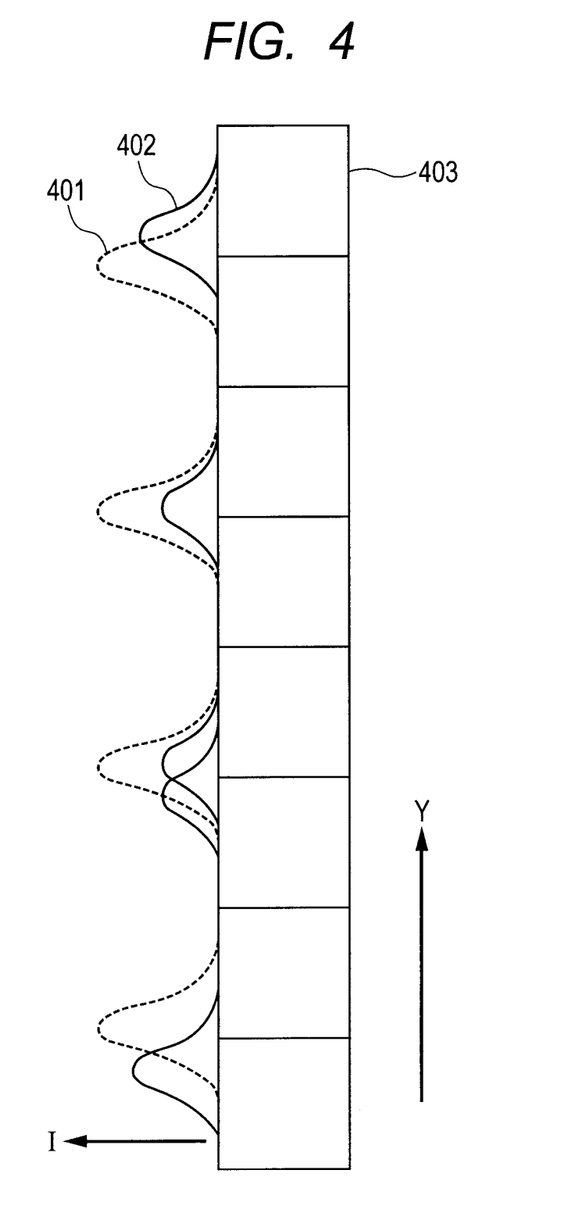
FIG. 4 is a schematic illustration of a part of the detector of Embodiment 1.

FIG. 4 is a schematic illustration of a part of the detector 105. FIG. 4 shows a part of the detector 105 as viewed in the X-direction in FIG. 1. In FIG. 4, reference X-rays 401 are those produced by splitting in a state where no detection object 104 exists. Each of them is discretely irradiated over two pixels out of the pixels 403 of the detector 105. X-rays 402 are those refracted as they are transmitted through a detection object 104. Each of the X-rays 402 is refracted relative to the corresponding reference X-ray 401 to change its position at which each of the X-rays strikes the detector 105 and shows an integrated intensity that is reduced due to absorption by the detection object 104.

If the X-ray intensities detected by the two pixels irradiated by a reference X-ray 401 are $I_{01}$ and $I_{02}$ respectively and the X-ray intensities detected by the two pixels irradiated by the corresponding X-ray 402 are $I_{11}$ and $I_{12}$ respectively, the X-ray transmittance A is expressed by Math (1) shown below:

Math. 1

$$A = \frac{I_{11} + I_{12}}{I_{01} + I_{02}} \quad (1)$$

On the other hand, as for the quantity of positional change ΔY, the splitting element 103 or the X-ray source 101 and the splitting element 103 are moved in the Y-direction relative to the detector 105 in a state where no detection object 104 exists and the X-ray intensity detected by each pixel is recorded.

Then, a data table that shows quantity B (ΔY) representing the ratio of the intensity detected by each pixel to the total intensity of an X-ray as expressed by Math (2) shown below relative to the quantity of positional change in the Y-direction ΔY on the detector 105 is prepared.

With these, the value of B(ΔY) can be computed from the quantity of positional change ΔY of an X-ray due to the refraction that takes place in a state where a detection object 104 exists and the intensity of the X-ray detected by each of the corresponding pixels. When preparing the data table, a single hole having a size equivalent to that of the apertures of the splitting element 103 may be used and the intensity of the transmitted X-ray may be detected at each position of the detector 105 instead of moving the splitting element 103.

Math. 2

$$B(\Delta Y) = \frac{I_{01}(\Delta Y)}{I_{01}(\Delta Y) + I_{02}(\Delta Y)} \quad (2)$$

or $$B(\Delta Y) = \frac{I_{02}(\Delta Y)}{I_{01}(\Delta Y) + I_{02}(\Delta Y)}$$

Now, the computationally processing method of this embodiment will be described.

Figure 5:
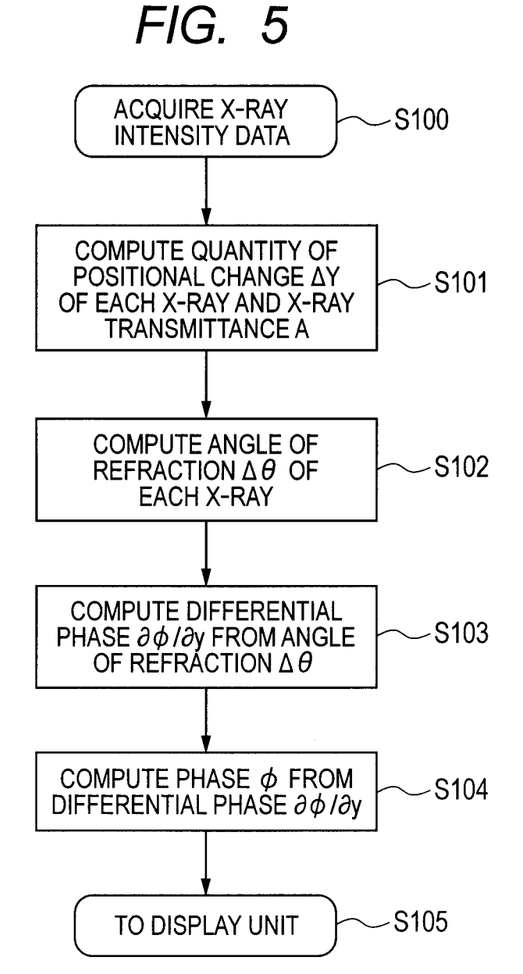
FIG. 5 is a flowchart of the computationally processing method of Embodiment 1.

FIG. 5 is a flowchart of the computational process of this embodiment. Firstly, in S100, information on the intensities of the transmitted X-rays that correspond to the respective positions of the detection object 104 are acquired while scanning X-rays over the detection object 104 or scanning the detection object 104 relative to the X-rays.

Then, in S101, the X-ray transmittance A is computed from the information on the intensities of the pixels in the Y-direction relative to the respective X-rays by using the computing unit 109 and the quantity B(ΔY) representing the ratio of the intensity detected by each pixel to the total intensity of the corresponding X-ray is computationally determined.

Subsequently, the quantities of positional changes (ΔY) are computed by using the database on quantities of positional changes (ΔY) and changes of X-ray intensities relative to the reference X-rays 401.

Alternatively, the data of B(ΔY) computationally obtained from the intensities that are observed by using reference X-rays may be made to fit by a function and the quantities of positional changes (ΔY) may be determined by using that function.

Thereafter, in S102, the angle of refraction (Δθ) of each X-ray is computed. The angle of refraction (Δθ) of each X-ray can be obtained by using the quantities of positional changes (ΔY) and the distance (Z) between the detection object 104 and the detector 105 and Math (3) shown below:

Math. 3

$$\Delta\theta = \tan^{-1}\frac{\Delta Y}{Z} \quad (3)$$

The relationship between the angle of refraction (Δθ) and the differential phase (∂ø/κy) is expressed by Math (4) shown below:

Math. 4

$$\frac{\partial \varphi}{\partial y} = \frac{2\pi}{\lambda}\Delta\theta \quad (4)$$

where λ is the wavelength of X-ray, which refers to the effective wavelength when a continuous X-ray is employed.

Then, in S103, the differential phase (∂ø/∂y) of each X-ray in the Y-direction is computed by means of the above Math (4) to acquire information on the differential phases.

In S104, phase information (ø) is obtained by integrating the differential phases (∂ø/∂y) obtained by way of the above-described computations in the Y-direction.

Note that a transmittance contrast image, a differential phase contrast image and a phase contrast image that are computationally determined in the above-described manner can be displayed in Step S105 by means of the display unit 112. The quantities B (ΔY), each of which shows the ratio of the intensity detected by each pixel to the total intensity of the corresponding X-ray, may be directly displayed as an image of the changes of the centers of gravity of the X-rays, or a center of gravity displacement image. The above-described arrangement can reduce the volume in the detection object 104 that contributes to scattering X-rays to by turn reduce the ratio of scattered X-rays relative to the detected X-ray intensities because finely split X-rays are scanned.

Additionally, an absorption image (transmittance contrast image) of a detection object 104, a center of gravity displacement image, a differential phase contrast image and a phase contrast image can be obtained by scanning in a direction perpendicular to the direction of X-ray splitting cycle because the change of the center of gravity of the X-ray in the splitting direction can be detected.

Other Configuration Examples

While the quantity of positional change of an X-ray is determined by means of 2 pixels in this embodiment as shown in FIG. 3, it may alternatively be determined by means of 3 or more than 3 pixels.

Figure 11:
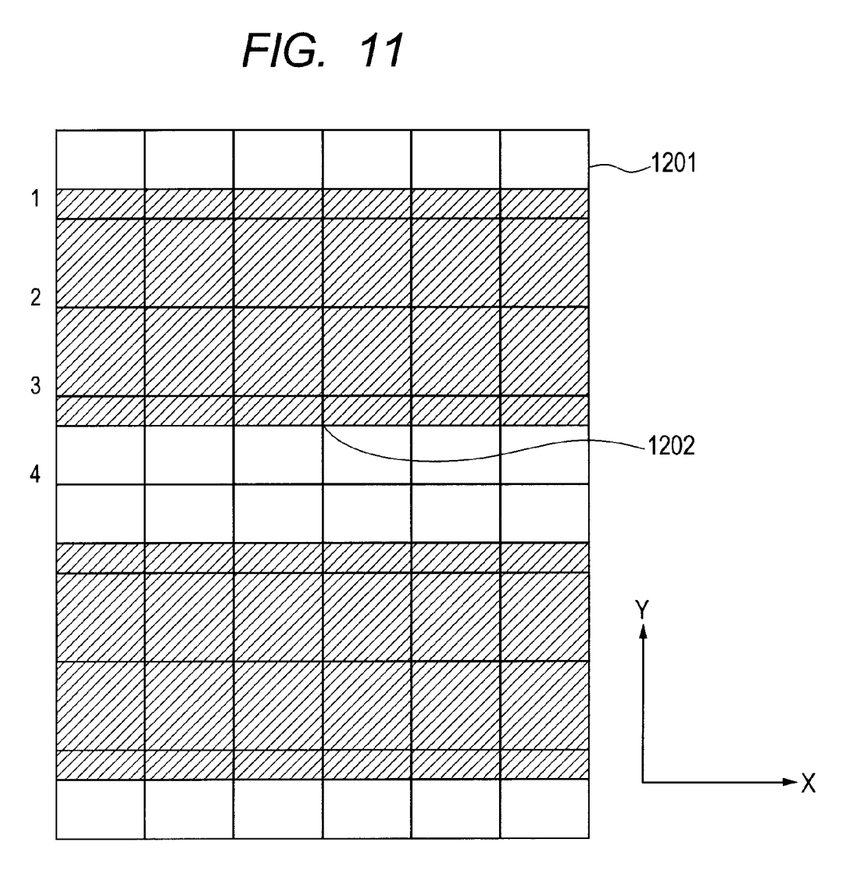
FIG. 11 is a schematic illustration of a part of the detector.

For example, FIG. 11 shows an instance where an incident X-ray 1202 strikes four pixels 1201 and the position of center of gravity in the Y-direction can be determined from intensity information at pixels 1 and 2 and at pixels 3 and 4.

Figure 12:
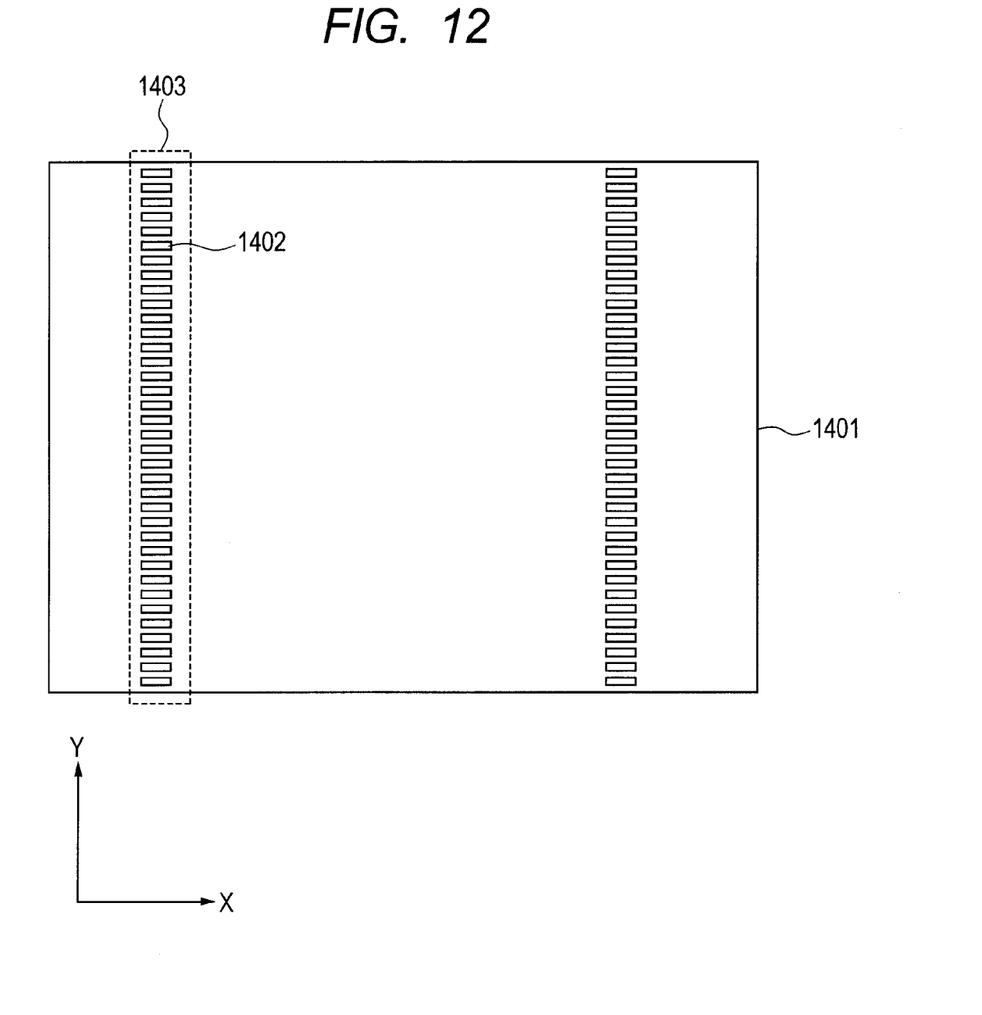
FIG. 12 is a schematic illustration of the splitting element.

FIG. 12 shows an instance of employing a splitting element formed by arranging a plurality of slit arrays 1403 in the X-direction. In the slit arrays 1403, holes 1402 for transmitting X-rays are formed periodically in the Y-direction. By arranging a plurality of slit arrays in the X-direction at intervals in this way, the quantity of the scattered X-ray that is produced as an X-ray is irradiated onto a detection object through one of the holes so as to influence the parts for detecting information on the next slit arrays of the detector can be limited. Additionally, by arranging a plurality of slit arrays 1403 in the X-direction at intervals, the scanning range can be limited to about the interval to by turn reduce the imaging time. The interval of the slit arrays 1403 is preferably not less than twice of the width of the slit arrays 1403 in the X-direction.

Embodiment 2

Now, a method of detecting the positional change of an X-ray in the X-direction simultaneously with the positional change thereof in the Y-direction will be described below by way of Embodiment 2. The basic configuration of this embodiment is identical with that of Embodiment 1 illustrated in FIG. 1.

Figure 6:
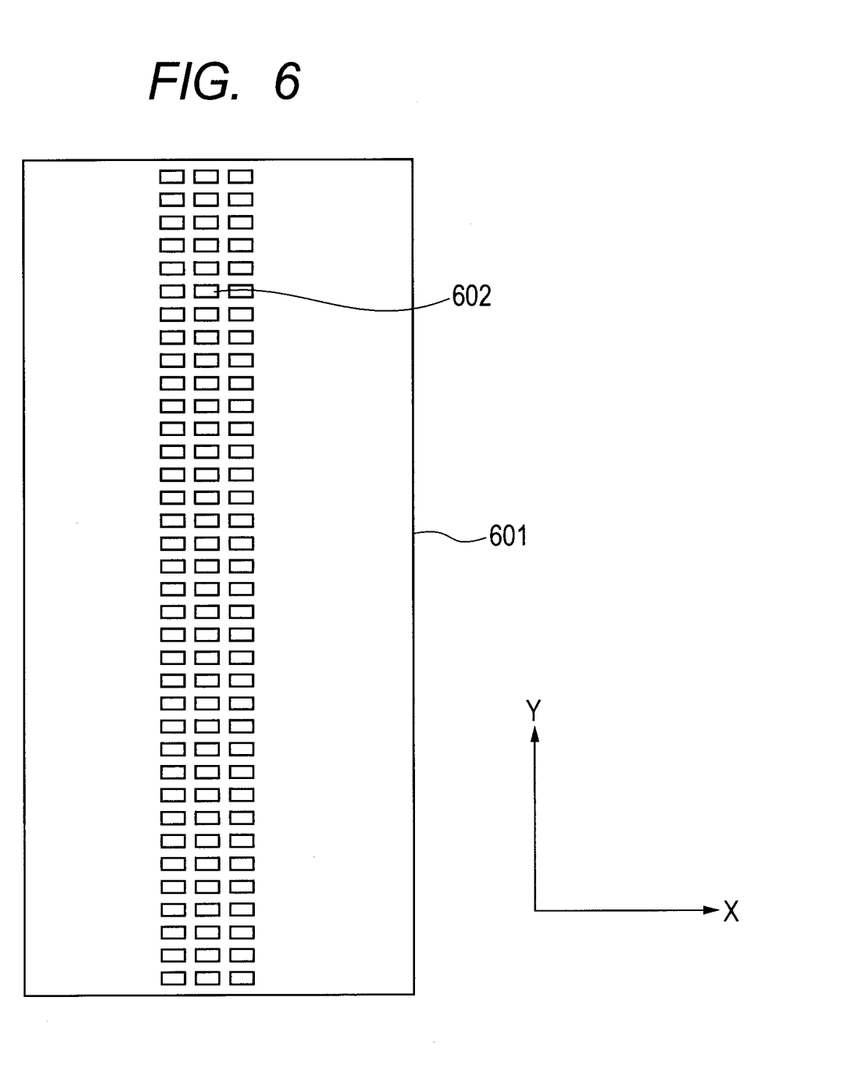
FIG. 6 is a schematic illustration of the splitting element according to Embodiment 2 of the present invention.

FIG. 6 is a schematic illustration of the splitting element 103 of Embodiment 2. The element has a basic structure formed by cutting holes 602 through the base material 601 periodically in the direction of the Y-axis so as to allow X-rays to pass through them. Such a periodic basic structure is also formed in the direction of the X-axis.

The holes 602 may not necessarily be cut through the base material of the optical element so long as X-rays can be transmitted through them. While the holes 602 are provided as an array of slits to form a line and space pattern, they may alternatively be circular holes.

The X-rays produced as the generated X-rays are split by the splitting element 103 are refracted by the detection object 104. The X-rays that are transmitted through the detection object 104 are then irradiated onto detector 105 having a spatial resolution. Thus, the splitting element 103 splits X-rays in the first direction (Y-direction) that is perpendicular to the optical axis direction of the X-ray and also in the second direction (X-direction) that is perpendicular to the optical axis direction of the X-ray and the first direction.

Figure 7:
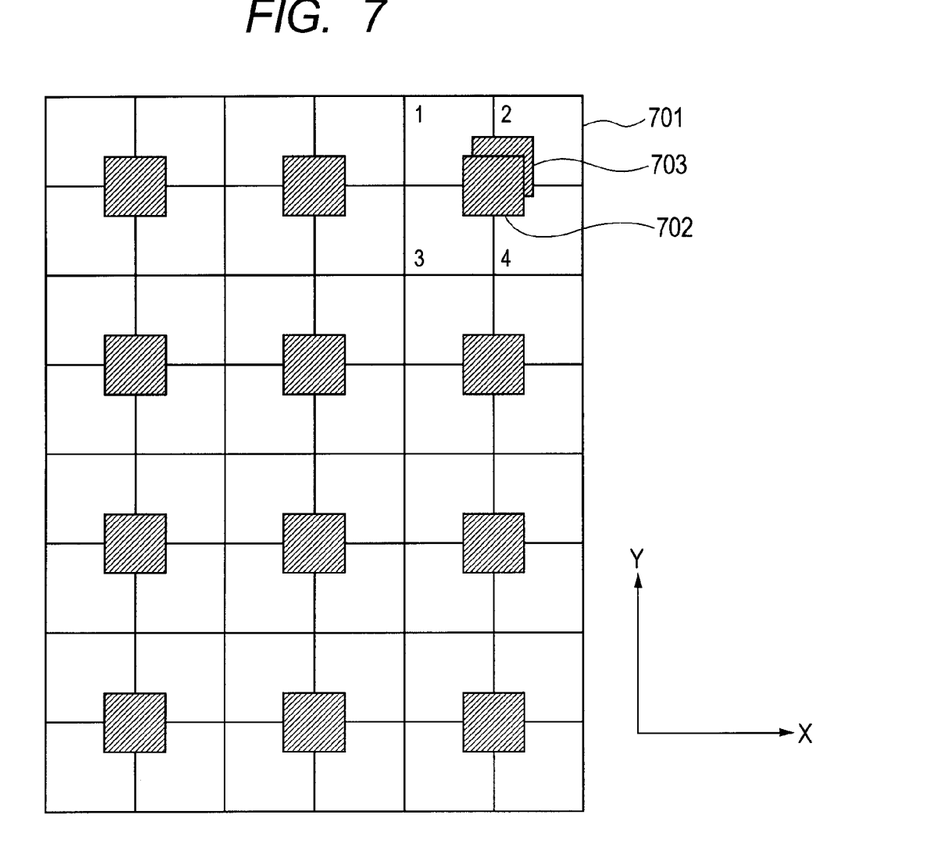
FIG. 7 is a schematic illustration of a part of the detector of Embodiment 2.

FIG. 7 schematically illustrates the detector 105. The detector 105 is formed by a plurality of pixels 701. Each of the reference X-rays 702 produced as the generated X-rays are split by the splitting element 103 is discretely irradiated over two pixels that are arranged in the X-direction and also over two pixels that are arranged in the Y-direction out of the pixels 701. Reference X-rays 702 are those produced by splitting in a state where no detection object 104 exists. The detector 105 detects the intensity of each of the irradiated X-rays at each of the pixels.

The X-ray source 101, the splitting element 103 and the detector 105 have respective transport units 106, 107 and 108. The X-ray detector 105 has an exposure control unit 109. The X-ray detector 105 can operate in the following manner, using transport control unit 110 and the exposure control unit 109. The X-ray detector 105 can acquire information on the entire detection object 104, synchronizing the moving time of the X-ray source 101, the splitting element 103 and the detector 105 in the X-direction and the image acquisition time of the detector 105.

Alternatively, the detection object 104 may be provided with a transport unit and the moving time of the detection object 104 on the X-axis and the image acquisition time of the detector 105 may be synchronized to obtain information on the entire detection object 104.

Furthermore, if the field of view of the detector 105 covers the region of observation of the detection object 104, the detector 105 may be rigidly held and information on the entire detection object 104 may be obtained by synchronizing the moving time of the X-ray source 101 and the splitting element 103 and the image acquisition time of the detector 105.

The information on the X-rays obtained by the detector 105 is numerically processed by the computing unit 111 and output to display unit 112 that may be a monitor.

Any of various detectors including those of the indirect type and those of the direct type may be used for the detector 105. Examples of detectors that can be used for the purpose of the present invention include X-ray flat panel detectors, X-ray CCD cameras and other direct conversion type two-dimensional X-ray detectors.

Now, detection of a phase shift of an X-ray caused by a detection object 104 will be described.

Reference X-rays 702 are those produced by splitting in a state where no detection object 104 exists. Each of them is irradiated over two pixels in the X-direction and also over two pixels in the Y-direction out of the pixels 701 of the detector 105 (pixel 1 through pixel 4). X-rays 703 are those refracted as they are transmitted through a detection object 104. Each of the X-rays 703 is refracted relative to the corresponding reference X-ray 702 to change its position at which it strikes the detector 105 and shows an integrated intensity that is reduced due to absorption by the detection object 104.

If the X-ray intensities detected by the four pixels including pixel 1 through pixel 4 that are irradiated by a reference X-ray 702 are $I_{01}$, $I_{02}$, $I_{03}$ and $I_{04}$ respectively and the X-ray intensities detected by the four pixels irradiated by the corresponding X-ray 703 are $I_{11}$, $I_{12}$, $I_{13}$ and $I_{14}$ respectively, the X-ray transmittance A is expressed by Math (5) shown below:

Math. 5

$$A = \frac{I_{11} + I_{12} + I_{13} + I_{14}}{I_{01} + I_{02} + I_{03} + I_{04}} \quad (5)$$

On the other hand, as for the quantities of positional changes $\Delta X$ and $\Delta Y$ relative to the X- and Y-directions respectively, the splitting element 103 or the X-ray source 101 and the splitting element 103 are moved in the X- and Y-directions relative to the detector 105 in a state where no detection object 104 exists and the X-ray intensity detected by each pixel is recorded.

Then, a data table that shows quantities $Bx(\Delta X)$ and $By(\Delta Y)$ representing the values of Maths (6) and (7) shown below relative to the quantities of positional changes in the X-direction and in the Y-direction, or $\Delta X$ and $\Delta Y$, on the detector 105 is prepared.

With these, the values of $Bx(\Delta X)$ and $By(\Delta Y)$ can be computed from the quantities of positional changes $\Delta X$ and $\Delta Y$ of an X-ray due to the refraction that takes place in a state where a detection object 104 exists and the intensity of the X-ray detected by each of the corresponding pixels.

When preparing the data table, a single hole having a size equivalent to that of the apertures of the splitting element 103 may be used and the intensity of the transmitted X-ray may be detected at each position of the detector 105 instead of moving the splitting element 103.

Math. 6

$$B_x(\Delta X) = \frac{I_{01}(\Delta X) + I_{03}(\Delta X)}{I_{01}(\Delta X) + I_{02}(\Delta X) + I_{03}(\Delta X) + I_{04}(\Delta X)} \quad (6)$$

or $$B_x(\Delta X) = \frac{I_{02}(\Delta X) + I_{04}(\Delta X)}{I_{01}(\Delta X) + I_{02}(\Delta X) + I_{03}(\Delta X) + I_{04}(\Delta X)}$$

Math. 7

$$B_y(\Delta Y) = \frac{I_{01}(\Delta Y) + I_{02}(\Delta Y)}{I_{01}(\Delta Y) + I_{02}(\Delta Y) + I_{03}(\Delta Y) + I_{04}(\Delta Y)} \quad (7)$$

or $$B_y(\Delta Y) = \frac{I_{03}(\Delta Y) + I_{04}(\Delta Y)}{I_{01}(\Delta Y) + I_{02}(\Delta Y) + I_{03}(\Delta Y) + I_{04}(\Delta Y)}$$

Figure 8:
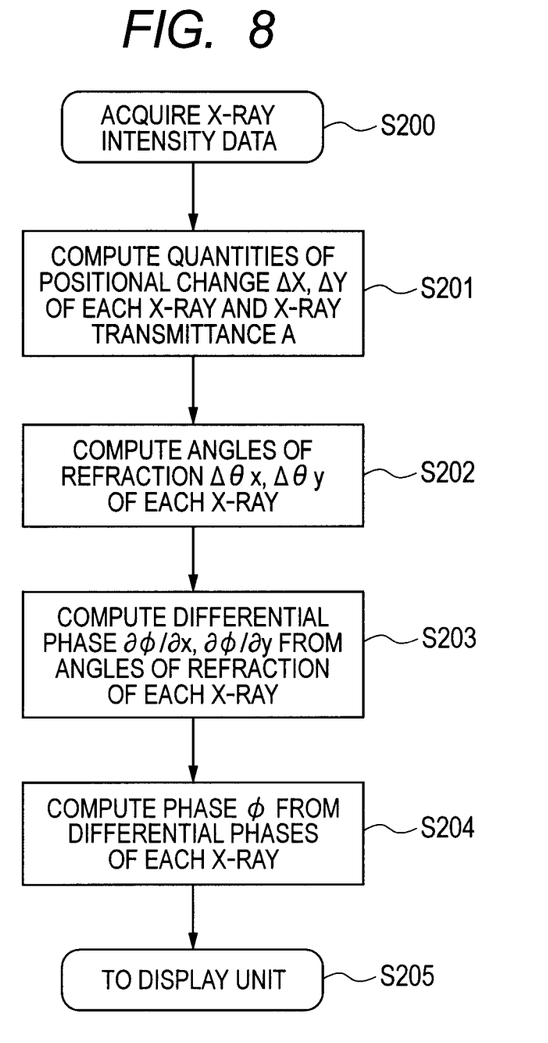
FIG. 8 is a flowchart of the computationally processing method of Embodiment 2.

Now, the computationally processing method of this embodiment will be described. FIG. 8 is a flowchart of the computational process of this embodiment.

Firstly, in S200, information on the intensities of the transmitted X-rays that correspond to the respective positions of the detection object 104 are acquired while scanning X-rays over the detection object 104 or scanning the detection object 104 relative to the X-rays.

Then, in S201, the X-ray transmittance A is computed from the information on the intensities of the pixels in the X-direction and in the Y-direction relative to the respective X-rays 703 by using the computing unit 111. Then, the quantities $Bx(\Delta X)$ and $By(\Delta Y)$ representing respectively the ratios of the intensities detected by the two pixels in the X-direction to the total intensity of the corresponding X-ray and that of the intensities of the two pixels in the Y-direction to the total intensity are computationally determined and the quantities of positional changes ($\Delta X$, $\Delta Y$) are computed by using the database on positional changes ($\Delta X$, $\Delta Y$) and changes of X-ray intensities relative to the reference X-rays 702.

Alternatively, the corresponding respective relationships between $Bx(\Delta X)$ and $By(\Delta Y)$ and $\Delta X$ and $\Delta Y$ may be made to fit in by a function and the quantities of positional changes ($\Delta X$, $\Delta Y$) may be determined by using the function.

Thereafter, in S202, the angles of refraction ($\Delta \theta x$, $\Delta \theta x$) of each X-ray relative to the X- and Y-directions are computed as in Embodiment 1.

Then, in S203, the differential phases ($\partial \phi / \partial x$, $\partial \phi / \partial y$) of each X-ray in the X-direction and in the Y-direction are computed to acquire information on the differentia phases of the X-rays.

In S204, phase information ($\phi$) is obtained by integrating the differential phases obtained by way of the above-described computations.

As for the integration, each pair of differential phases may be integrated separately or, alternatively, the integration may be done as a Fourier integral using $\partial \phi / \partial x$ and $\partial \phi / \partial y$. Note that a transmittance contrast image, a differential phase contrast image and a phase contrast image that are computationally determined in the above-described manner can be displayed in Step S205 by means of the display unit 112. The quantities $Bx(\Delta X)$, $By(\Delta Y)$, which show the ratios of the intensities detected by each pair of pixels in the X-direction and those detected by each pair of pixels in the Y-direction to the total intensity of the corresponding X-ray may be directly displayed as an image of the changes of the centers of gravity of the X-rays, or a center of gravity displacement image.

The above-described arrangement can reduce the volume in the detection object 104 that contributes to scattering X-rays to by turn reduce the ratio of scattered X-rays relative to the detected X-ray intensities because finely split X-rays are scanned. Additionally, since the splitting element 103 has a periodic structure also in the scanning direction, the change in the center of gravity of each X-ray in the scanning direction can also be detected.

Thus, with the above-described arrangement of this embodiment, it is possible to obtain an absorption image (transmittance contrast image) of a detection object 104 and a center of gravity displacement image (X-direction, Y-direction), a differential phase contrast image (X-direction, Y-direction) and a phase contrast image of X-rays.

Embodiment 3

A method using a pulse X-ray and a time delay integration (TDI) type detector (to be referred to as TDI detector hereinafter) will be described below by way of Embodiment 3. With this method, the quantity of positional change of an X-ray in the Y-direction and also the quantity of positional change of the X-ray in the X-direction can be observed at the same time.

Figure 9:
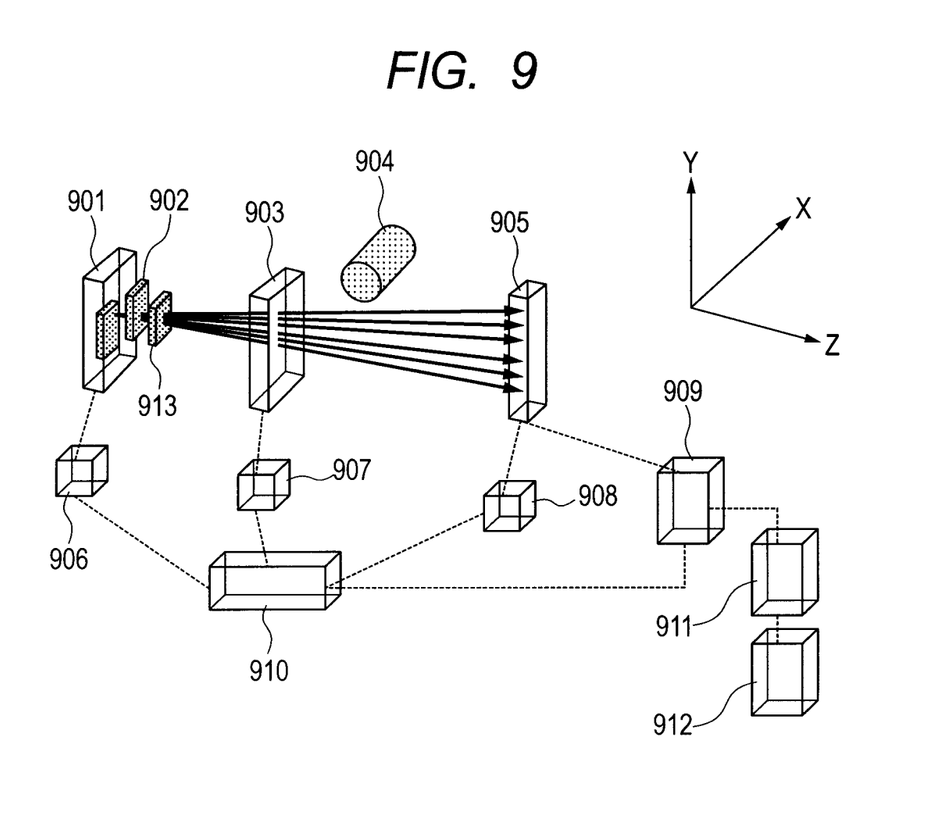
FIG. 9 is a schematic illustration of a configuration example of the X-ray imaging apparatus according to Embodiment 3 of the present invention.

FIG. 9 is a schematic illustration of a configuration example of the X-ray imaging apparatus of this embodiment. Divergence of the X-ray generated from the X-ray source 901 that is an X-ray generating unit is limited by means of a slit 902 or the like. The slit 902 may be integrally formed with the X-ray source 901. The X-ray generated from the X-ray source 901 is made to be pulse-shaped by X-ray pulse irradiation unit 913 so as to be irradiated onto a detection object 904 in a temporally pulse-shaped manner.

More specifically, the X-ray pulse irradiation unit 913 is a rotary shutter that transmits an X-ray of a predefined frequency. Note, however, that the X-ray pulse irradiation unit 913 may not necessarily be provided if the X-ray source 901 is capable of operating for pulse irradiations. For example, the X-ray emitted from the X-ray source 901 can be electrically controlled or a rotating anticathode type X-ray source is used to arrange the X-ray generating substance of the rotating target part thereof at regular intervals relative to the sense of rotation.

With such an arrangement, a pulse-shaped X-ray can be generated as a function of the rotational speed and the cycle of arrangement of the target substance of the rotating target. For the purpose of the present patent application, an X-ray source operating for pulse irradiation is generally referred to as an "X-ray generating unit for generating a pulse-shaped X-ray" regardless of whether an X-ray pulse irradiation unit 913 is employed, it is electrically controlled or a rotating anticathode is used.

Then, the pulse X-rays whose divergence is suppressed are spatially split in the X- and Y-directions by the splitting element 903 and transmitted through a part of the detection object 904.

The splitting element 903 is similar to the one used in Embodiment 2. The split X-rays produced from the splitting element 903 are refracted by the detection object 904. The X-rays transmitted through the detection object 904 are irradiated onto the X-ray TDI detector 905.

While the signal quantity of each pixel is output at each exposure by an ordinary CCD, the electric charge of each pixel is vertically transferred on a column by column basis for reading by means of a TDI type CCD. Then, the CCD can be operated for integrated exposure for the number of columns by synchronizing the electric charge transfer speed and the moving speed of the detection object 904 (the X-ray scanning speed). Thus, a high quality image of the detection object 904 that is moving at high speed can be obtained practically without any blur as compared with ordinary two-dimensional detectors. The imaging time should be reduced particularly for medical applications.

When a TDI type detector is employed, the positional displacement of an X-ray in a direction (Y) perpendicular to the scanning direction (X) can be detected by the method of Embodiment 2 that uses X-rays being continuously irradiated onto a detection object 904. However, this method cannot detect any positional displacement in the scanning direction (X).

Figure 10:
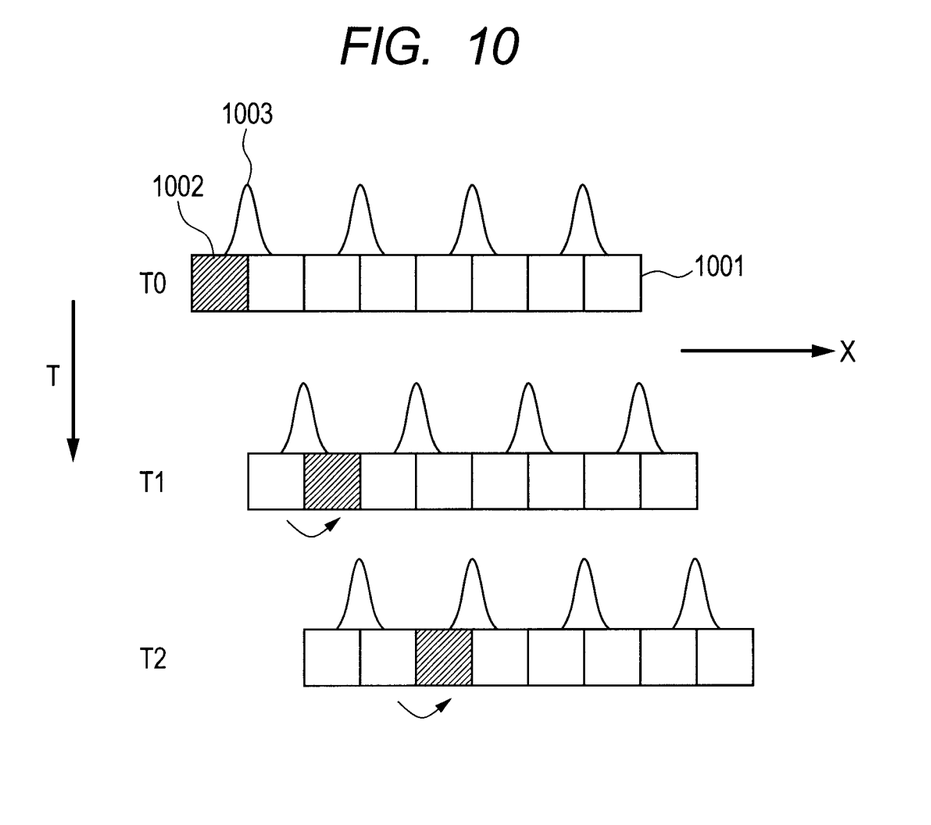
FIG. 10 is a schematic illustration of the mode of operation of the detector of the X-ray imaging apparatus of Embodiment 3.

FIG. 10 schematically illustrates this fact. FIG. 10 shows detector part 1001 of a row in the X-direction of an X-ray TDI detector 905. FIG. 10 shows an X-ray 1003 that is produced as a generated X-ray is split by the splitting element 903 is irradiated over two pixels 1002. Then, the X-ray 1003 and the detector part 1001 are scanned in synchronism with each other by means of a transport control unit 910 and an exposure control unit 909 to obtain intensity information on the X-ray 1003. To detect the center of gravity of the X-ray in the X-direction, the ratio of the intensity of the left pixel and that of the intensity of the right pixel relative to the total intensity of the two pixels being irradiated by the X-ray are determined However, when an X-ray TDI detector 905 is employed, the electric charge stored in each pixel is transferred to the next pixel in the X-direction at timing T1. Therefore, the intensity of the X-ray that is ultimately obtained is the integrated intensity of the two pixels arranged side by side so that the center of gravity in the X-direction cannot be detected.

When, on the other hand, a pulse X-ray is employed and the irradiation of the X-ray is turned ON/OFF at timings (T1, T2) of transferring an electric charge, the electric charge transferred from the pixel 1002 that is irradiated with the X-ray at the time of starting a measurement constantly conveys information on the X-ray 1003 in the left side region if the above ON/OFF operation is repeated for imaging.

Similarly, the electric charge transferred from the pixel next to the pixel 1002 at the right side of the latter constantly conveys information on the intensity of the X-ray in the right side region. In this way, the intensity of the X-ray at the left side pixel and that of the X-ray at the right side pixel can ultimately be detected in an independent manner.

Thus, the center of gravity of the X-ray can be detected not only in the Y-direction but also in the X-direction by using an X-ray TDI detector when the cycle period of the X-ray pulse and that of the electric charge transfer are synchronized with each other. Note that the cycle period of pulse irradiation needs to be synchronized with the cycle period of the electric charge transfer of the X-ray TDI detector 905.

The X-ray pulse irradiation unit 913 is moved by means of a transport unit 906 if the X-ray pulse irradiation unit 913 is integrated with the X-ray source 901, although a separate transport unit may be provided if the X-ray pulse irradiation unit 913 is separated from the X-ray source 901. The X-ray TDI detector 905 has an exposure control unit 909 and information can be acquired by means of a transport control unit 910, the exposure control unit 909 and a pulse control unit 912 in a manner as described below.

Information on the entire detection object 904 can be acquired by synchronizing the moving speed of the X-ray source 901, the splitting element 903 and the X-ray TDI detector 905 in the X-direction and the cycle period of the pulse irradiation and that of the electric charge transfer of the X-ray TDI detector 905.

The transfer movements by the transport units 906, 907 and 908 may be circular movements centered at the X-ray source 901.

The moving speed of the X-ray source 901, the splitting element 903 and the X-ray TDI detector 905, the cycle period of the pulse irradiation by the X-ray pulse irradiation unit 913 and that of the electric charge transfer of the X-ray TDI detector 905 are synchronized. They may alternatively be arranged in the following manner instead of acquiring information on the entire detection object 904 in the above-described manner.

Namely, the detection object 904 is provided with a transport unit and information on the entire detection object 904 is acquired by synchronizing the cycle period of the transfer of the detection object 904 in the X-axis direction, that of the pulse irradiation by the X-ray pulse irradiation unit 913 and that of the electric charge transfer of the X-ray TDI detector 905 by the exposure control unit 909.

The information on the X-rays obtained by the X-ray TDI detector 906 is numerically processed by computing unit 911 and output to display unit 912 that may be a monitor. An absorption image (transmittance contrast image) of a detection object 104, a center of gravity of the X-ray due to refraction, a differential phase contrast image and a phase contrast image can be acquired by computations similar to those of Embodiment 2.

The above-described arrangement can reduce the volume in the detection object 904 that contributes to scattering X-rays to by turn reduce the ratio of scattered X-rays relative to the detected X-ray intensities because finely split X-rays are scanned.

Additionally, an imaging operation can be conducted at a higher speed by using an X-ray TDI detector 905 as compared with the use of some other detector. Furthermore, a shift of the center of gravity can be detected not only in a direction perpendicular to the scanning direction but also in a direction parallel to the scanning direction by pulse X-ray irradiation. Thus, a differential phase contrast image can be obtained in two directions to increase the quantity of information that can be acquired.

A splitting element described for any of the preceding embodiments may also be employed for the splitting element of this embodiment.

This application claims the benefit of Japanese Patent Application No. 2009-276521, filed Dec. 4, 2009, which is hereby incorporated by reference herein in its entirety.

REFERENCE SIGNS LIST

101: X-ray source
102: slit
103: splitting element
104: detection object
105: detector
106: transport unit
107: transport unit
108: transport unit
109: exposure control unit
110: transport control unit
111: computing unit
112: display unit

The invention claimed is:

1. An X-ray imaging apparatus comprising:
an X-ray generating unit for generating pulse-shaped X-rays;
a splitting element that spatially splits X-rays generated by said X-ray generating unit;
a detecting unit that detects intensity of each of the split X-rays split by said splitting element and transmitted through a detection object;
a transport unit that moves said X-ray generating unit, said splitting element, the detection object or said detecting unit; and
a transport control unit that controls a scanning time of the X-rays irradiated onto the detection object by means of said transport unit,
wherein said detecting unit comprises a time delay integration type detecting unit which has a plurality of pixel areas and is so arranged that each of the split X-rays split by said splitting element is discretely irradiated over two or more than two pixel areas of said detecting unit, and
wherein said X-ray generating unit and said detecting unit operate with a cycle period of X-ray pulse generation and with a cycle period of electric charge transfer, respectively, and wherein those periods are synchronized such that X-rays are irradiated onto the detection object between timing T0 and timing T1 and X-rays are not irradiated onto the detection object between timing T1 and timing T2 while electric charge transfer is performed in said detecting unit at the timings T0, T1 and T2.

2. The apparatus according to claim 1, wherein a first part of said plurality of pixel areas transfer an electric charge generated only by an intensity of X-rays in that first part of said plurality of pixel areas, and at least a second part of said pixel areas other than said first part of said pixel areas transfer an electric charge generated only by an intensity of X-rays in said second pixel areas.

3. The apparatus according to claim 1, wherein said detecting unit independently detects an intensity of X-rays irradiated onto a single pixel area of said detecting unit and an intensity of X-rays irradiated onto a pixel area or pixel areas adjacent to said single pixel area.

4. The apparatus according to claim 1, wherein the scanning direction of X-rays irradiated onto the detection object is the same as the direction of electric charge transfer in said detecting unit.

5. The apparatus according to claim 1, wherein said splitting element spatially splits X-rays with respect to two directions.

6. The apparatus according to claim 1, wherein said splitting element spatially splits X-rays in a first direction perpendicular to the optical axis direction of the X-rays and in a second direction perpendicular to the optical axis direction of the X-rays and the first direction.

7. The apparatus according to claim 1, further comprising a computing unit that computes a quantity of positional change from information acquired by said detecting unit.

8. The apparatus according to claim 1, further comprising a computing unit that computes a differential phase contrast image or a phase contrast image of the detection object from the information acquired by said detecting unit.

9. The apparatus according to claim 1, further comprising an exposure control unit that synchronizes the scanning time of the X-rays and an image acquisition time of said detecting unit.

10. An X-ray imaging method comprising the steps of:
spatially splitting pulsed-shaped X-rays generated by an X-ray generating unit;
irradiating the spatially split X-rays onto a detection object; and
detecting the intensity of the X-rays transmitted through the detection object by means of a detecting unit, while synchronizing a scanning time of irradiating X-rays onto the detection object and an image acquisition time of the detecting unit,
wherein the detecting unit is a time delay integration type detecting unit which has a plurality of pixel areas and each of the split X-rays is discretely irradiated over two or more than two pixel areas of the detecting unit, and
wherein the X-ray generating unit and the detecting unit operate with a cycle period of X-ray pulse generation and with a cycle period of electric charge transfer, respectively, and wherein those periods are synchronized such that X-rays are irradiated onto the detection object between timing T0 and timing T1 and X-rays are not irradiated onto the detection object between timing T1 and timing T2 while electric charge transfer is performed in the detecting unit at the timings T0, T1 and T2.

11. The method according to claim 10, wherein the detecting unit is a detecting unit for vertically transferring an electric charge of each of the pixels column by column and an electric charge transferring speed of the vertical transfer and a scanning speed of the X-rays are synchronized.

12. The method according to claim 10, wherein a first part of the plurality of pixel areas transfer an electric charge generated only by an intensity of X-rays in that first part of the plurality of pixel areas, and at least a second part of pixel areas that is other than the first part of the plurality of pixel areas transfer an electric charge generated only by an intensity of X-rays in that second part of the pixel areas.

13. The method according to claim 10, wherein the detecting unit independently detects an intensity of X-rays irradiated onto a single pixel area of the detecting unit and an intensity of X-rays irradiated onto a pixel area or pixel areas adjacent to the single pixel area.

* * * * *